US009003538B2

(12) United States Patent
Markisohn et al.

(10) Patent No.: US 9,003,538 B2
(45) Date of Patent: Apr. 7, 2015

(54) METHOD AND SYSTEM FOR ASSOCIATING DATABASE CONTENT FOR SECURITY ENHANCEMENT

(75) Inventors: David Bradley Markisohn, Indianapolis, IN (US); Igor Gejdos, Indianapolis, IN (US); Morris J. Young, Indianapolis, IN (US); Keith E. Bernard, Fort Wayne, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1169 days.

(21) Appl. No.: 11/999,951

(22) Filed: Dec. 7, 2007

(65) Prior Publication Data

US 2009/0150683 A1 Jun. 11, 2009

(51) Int. Cl.
*G06F 21/62* (2013.01)
*G06Q 50/24* (2012.01)
*G06F 19/00* (2011.01)

(52) U.S. Cl.
CPC .......... *G06F 19/322* (2013.01); *G06F 21/6245* (2013.01); *G06F 21/62* (2013.01); *G06F 19/32* (2013.01); *G06Q 50/24* (2013.01)

(58) Field of Classification Search
None
See application file for complete search history.

(56) References Cited

U.S. PATENT DOCUMENTS

| | | | |
|---|---|---|---|
| 5,251,126 A | 10/1993 | Kahn et al. | |
| 5,497,486 A | 3/1996 | Stolfo et al. | |
| 5,671,404 A | 9/1997 | Lizee et al. | |
| 5,671,409 A | 9/1997 | Fatseas et al. | |
| 5,951,300 A | 9/1999 | Brown | |
| 5,995,962 A | 11/1999 | Horowitz | |
| 6,024,699 A | 2/2000 | Surwit et al. | |
| 6,032,119 A | 2/2000 | Brown et al. | |
| 6,322,502 B1 | 11/2001 | Schoenberg et al. | |
| 6,425,863 B1 | 7/2002 | Werner et al. | |
| 6,562,001 B2 | 5/2003 | Lebel et al. | |
| 6,564,105 B2 | 5/2003 | Starkweather et al. | |
| 6,571,128 B2 | 5/2003 | Lebel et al. | |

(Continued)

FOREIGN PATENT DOCUMENTS

| | | |
|---|---|---|
| DE | 20217855 | 2/2003 |
| EP | 0970655 | 1/2000 |

(Continued)

OTHER PUBLICATIONS

Wang, C. et al.; "*A CORBA-Based Object Framework with Patient Identification Translation and Dynamic Linking, Methods for Exchanging Patient Data*," Methods of Information in Medicine, Mar. 1999, pp. 56-65, vol. 38, No. 1, F.K.Schattauer Verlagsgesellschaft mbH, Germany.

(Continued)

*Primary Examiner* — Alexander Lagor
(74) *Attorney, Agent, or Firm* — Roche Diagnostics Operations, Inc.

(57) ABSTRACT

A system and method for associating database content for security enhancement is provided, the method being applicable to a system comprising a computer configured to process a data management application and to store data in databases. According to one embodiment of the method according to the invention, the application uses an encryption key to encrypt data. The application stores the encrypted data in two or more databases. The databases may comprise a system database for storing encrypted user access data and one or more results databases for storing patient data. Databases may be stored locally, remotely, or both locally and remotely.

10 Claims, 3 Drawing Sheets

(56) References Cited

U.S. PATENT DOCUMENTS

| | | | |
|---|---|---|---|
| 6,577,899 B2 | 6/2003 | Lebel et al. |
| 6,585,644 B2 | 7/2003 | Lebel et al. |
| 6,605,038 B1 | 8/2003 | Teller et al. |
| 6,635,014 B2 | 10/2003 | Starkweather et al. |
| 6,648,821 B2 | 11/2003 | Lebel et al. |
| 6,659,948 B2 | 12/2003 | Lebel et al. |
| 6,668,196 B1 | 12/2003 | Villegas et al. |
| 6,684,191 B1 | 1/2004 | Barnard et al. |
| 6,687,546 B2 | 2/2004 | Lebel et al. |
| 6,694,191 B2 | 2/2004 | Starkweather et al. |
| 6,733,446 B2 | 5/2004 | Lebel et al. |
| 6,740,075 B2 | 5/2004 | Lebel et al. |
| 6,748,402 B1 | 6/2004 | Reeves |
| 6,758,810 B2 | 7/2004 | Lebel et al. |
| 6,781,522 B2 | 8/2004 | Sleva et al. |
| 6,804,656 B1 | 10/2004 | Rosenfeld et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,852,104 B2 | 2/2005 | Blomquist |
| 6,873,268 B2 | 3/2005 | Lebel et al. |
| 6,873,807 B2 | 3/2005 | Umetsu |
| 6,958,705 B2 | 10/2005 | Lebel et al. |
| 6,990,434 B2 | 1/2006 | Minogue et al. |
| 7,020,508 B2 | 3/2006 | Stivoric et al. |
| 7,024,236 B2 | 4/2006 | Ford et al. |
| 7,029,455 B2 | 4/2006 | Flaherty |
| 7,041,468 B2 | 5/2006 | Drucker et al. |
| 7,050,735 B2 | 5/2006 | Bardolatzy et al. |
| 7,063,665 B2 | 6/2006 | Hasegawa et al. |
| 7,082,334 B2 | 7/2006 | Boute et al. |
| 7,113,946 B2 | 9/2006 | Cosic |
| 7,120,488 B2 | 10/2006 | Nova et al. |
| 7,165,062 B2 | 1/2007 | O'Rourke |
| 7,179,226 B2 | 2/2007 | Crothall et al. |
| 7,181,350 B2 | 2/2007 | Oberding et al. |
| 7,207,009 B1 | 4/2007 | Aamodt et al. |
| 2002/0010679 A1* | 1/2002 | Felsher ............ 705/51 |
| 2002/0016568 A1 | 2/2002 | Lebel et al. |
| 2002/0029776 A1 | 3/2002 | Blomquist |
| 2002/0040208 A1 | 4/2002 | Flaherty et al. |
| 2002/0059299 A1 | 5/2002 | Spaey |
| 2002/0140976 A1 | 10/2002 | Borg et al. |
| 2002/0193679 A1 | 12/2002 | Malave et al. |
| 2003/0002848 A1 | 1/2003 | Kawaoka et al. |
| 2003/0011646 A1 | 1/2003 | Levine et al. |
| 2003/0061358 A1* | 3/2003 | Piazza et al. ........ 709/227 |
| 2003/0065308 A1 | 4/2003 | Lebel et al. |
| 2003/0065536 A1 | 4/2003 | Hansen et al. |
| 2003/0069758 A1 | 4/2003 | Anderson et al. |
| 2003/0098869 A1 | 5/2003 | Arnold et al. |
| 2003/0140044 A1 | 7/2003 | Mok et al. |
| 2003/0145206 A1 | 7/2003 | Wolosewicz et al. |
| 2003/0163088 A1 | 8/2003 | Blomquist |
| 2003/0199739 A1 | 10/2003 | Gordon et al. |
| 2003/0208465 A1 | 11/2003 | Yurko et al. |
| 2004/0030987 A1 | 2/2004 | Manelli |
| 2004/0038389 A1 | 2/2004 | Maus et al. |
| 2004/0073464 A1 | 4/2004 | Huang |
| 2004/0086314 A1 | 5/2004 | Chen et al. |
| 2004/0111296 A1 | 6/2004 | Rosenfeld et al. |
| 2004/0119742 A1 | 6/2004 | Silbey et al. |
| 2004/0172284 A1 | 9/2004 | Sullivan et al. |
| 2005/0004947 A1 | 1/2005 | Emlet et al. |
| 2005/0010452 A1 | 1/2005 | Lusen |
| 2005/0137653 A1 | 6/2005 | Friedman et al. |
| 2005/0159977 A1 | 7/2005 | Green et al. |
| 2005/0182655 A1 | 8/2005 | Merzlak et al. |
| 2005/0187794 A1 | 8/2005 | Kimak |
| 2005/0192844 A1 | 9/2005 | Esler et al. |
| 2005/0228697 A1* | 10/2005 | Funahashi ............ 705/2 |
| 2005/0259945 A1 | 11/2005 | Splaver |
| 2006/0010014 A1 | 1/2006 | Brown |
| 2006/0020491 A1 | 1/2006 | Mongeon et al. |
| 2006/0031094 A1 | 2/2006 | Cohen et al. |
| 2006/0085347 A1* | 4/2006 | Yiachos ............ 705/51 |
| 2006/0095298 A1 | 5/2006 | Bina |
| 2006/0155581 A1 | 7/2006 | Eisenberger et al. |
| 2006/0161460 A1 | 7/2006 | Smitherman et al. |
| 2006/0167367 A1 | 7/2006 | Stanczak et al. |
| 2006/0178910 A1 | 8/2006 | Eisenberger et al. |
| 2006/0184524 A1 | 8/2006 | Pollanz |
| 2006/0224638 A1 | 10/2006 | Wald et al. |
| 2006/0272652 A1 | 12/2006 | Stocker et al. |
| 2007/0006322 A1* | 1/2007 | Karimzadeh et al. ........ 726/27 |
| 2007/0033074 A1 | 2/2007 | Nitzan et al. |
| 2007/0048691 A1 | 3/2007 | Brown |
| 2007/0055940 A1 | 3/2007 | Moore et al. |
| 2007/0088525 A1 | 4/2007 | Fotiades et al. |
| 2007/0089071 A1 | 4/2007 | Zinn et al. |
| 2007/0179352 A1 | 8/2007 | Randlov et al. |
| 2007/0179975 A1 | 8/2007 | Teh et al. |
| 2007/0185390 A1 | 8/2007 | Perkins et al. |
| 2007/0189590 A1 | 8/2007 | Fidrich et al. |
| 2007/0219432 A1 | 9/2007 | Thompson |
| 2007/0232866 A1 | 10/2007 | Nephin et al. |
| 2007/0245152 A1* | 10/2007 | Pizano et al. ............ 713/186 |
| 2007/0276197 A1 | 11/2007 | Harmon |

FOREIGN PATENT DOCUMENTS

| | | |
|---|---|---|
| EP | 0649316 | 12/2000 |
| EP | 1194864 | 4/2002 |
| EP | 1416417 | 5/2004 |
| EP | 1647929 | 4/2006 |
| EP | 1662417 | 5/2006 |
| JP | 04/145774 | 5/2004 |
| JP | 04/145775 | 5/2004 |
| JP | 04/145776 | 5/2004 |
| JP | 07/058685 | 3/2007 |
| WO | WO9609590 | 3/1996 |
| WO | WO0018449 | 4/2000 |
| WO | WO0065522 | 11/2000 |
| WO | WO0072181 | 11/2000 |
| WO | WO0174229 | 10/2001 |
| WO | WO0200111 | 1/2002 |
| WO | WO02078512 | 10/2002 |
| WO | WO03015838 | 2/2003 |
| WO | WO2005037095 | 4/2005 |
| WO | WO2005096206 | 10/2005 |
| WO | WO2006050485 | 5/2006 |
| WO | WO2007005530 | 1/2007 |
| WO | WO2007084502 | 7/2007 |
| WO | WO2007093482 | 8/2007 |

OTHER PUBLICATIONS

Bilenko, M. et al.; "*Adaptive Name Matching in Information Integration,*" IEEE Intelligent Systems; Sep. 2003, vol. 18, No. 5; p. 16-23, IEEE Computer Society.

Frenger, Paul; "*GRANNIE 2: a Ubiquitious, Protean Robotic Guardian Angel,*" Automation Science and Engineering, Sep. 1, 2007, pp. 857-862, IEEE International Conference on IEEE.

Frenger, Paul; "*GRANNIE: A Scalable, Interactive, Artificial Intelligence Supervisory System for Medical Devices,*" Proceedings of Can. Med. Bio. Engr. Conference, 2007, p. 256-259.

"CoPilot Health Management System Version 3.1," User's Guide, Mar. 2007, 230 pp., ART 10641 Rev. D, Abbott Diabetes Care, Inc.

"MediSense® Precision Link® Diabetes Data Management Software," User's Guide, May 2006, 58 pp., 116-412 Rev. AC, Abbott Diabetes Care, Inc.

Albisser, Michael A.; "A Graphical User Interface for Diabetes Management Than Integrates Glucose Prediction and Decision Support," Diabetes Technology & Therapeutics, 2005, pp. 264-273, vol. 7, No. 2.

Janssen et al., "Acensia® Winglucofacts® Professional Intelligent Diabetes Management Software Is an Effective Tool for the Management of Diabetes," Bayer HealthCare Clinical Summary Report, Jul. 2005, 10 pp.

(56) References Cited

OTHER PUBLICATIONS

Joshy et al.; "Diabetes Information Systems: A Rapidly Emerging Support for Diabetes Surveillance and Care," Diabetes Technology & Therapeutics, 2006, pp. 587-597, vol. 8, No. 5.
"OneTouch Diabetes Management Software," User Manual, 2006, 173 pp., v. 2.3.1, Lifescan, Inc.
"Getting Started, CareLink Personal Therapy Management Software for Diabetes," Brochure, 2007, 20 pp., Medtronic Minimed, Inc.
"Accu-Chek® Camit Pro Diabetes Management Software," User's Manual, 2005, 220 pp., v.2.1 and Addendum v. 2.4, Roche Diagnostics Corp.
"Accu-Chek® Compass Diabetes Care Software," User's Guide, 2005, 74 pp., Roche Diagnostics Corp.
"Accu-Chek® Diabetes Assistant," accessed with notional data and printed from www.diabetesassistant.com on Jan. 16, 2007, 20 pp., Roche Diagnostics Corp.
PCT International Search Report and Written Opinion of the International Search Authority for Pat. Appl. No. PCT/EP2008/009871.

* cited by examiner

METHOD AND SYSTEM FOR ASSOCIATING DATABASE CONTENT FOR SECURITY ENHANCEMENT

FIELD OF THE INVENTION

The present disclosure relates to a method and system for installing and operating software applications. More particularly, the disclosure relates to a method and system for associating database content to enhance security.

BACKGROUND OF THE INVENTION

Many fields of medical treatment and healthcare require monitoring of certain physiological parameters. Technological advancements in medicine led to the increased use of medical devices, e.g., meters and infusion pumps, to collect medical data, and of healthcare data management systems.

The sensitive nature of medical data requires security. Healthcare data management methods and systems traditionally developed for use in healthcare facilities and health management organizations are increasingly used by patients, care givers, and others. U.S. Pat. No. 7,103,578 and U.S. Published Application No. 2004/0172284 disclose two such methods and systems. Some healthcare data management systems are able to transfer data between them. Security must keep pace with broad use of healthcare data management systems of various configurations.

SUMMARY OF THE INVENTION

A system and method for associating database content for enhanced security is provided. The system comprises an application for managing data, a computer configured to process the application, an encryption key configured to encrypt data and two or more databases for storing encrypted data. The method may be performed in the system according to the invention.

In accordance with an aspect of the present invention, a method for associating database content for enhanced security is provided. The method comprises the steps of creating an encryption key, encrypting data with the encryption key, and storing encrypted data in two or more databases. In one embodiment, the databases can comprise a system database for storing encrypted user access data and one or more results databases for storing patient data. Databases may be stored locally, remotely, or both locally and remotely.

DESCRIPTION OF THE DRAWINGS

The foregoing aspects of this invention will become more readily appreciated as the same become better understood by reference to the following detailed description when taken in conjunction with the accompanying drawings.

Corresponding reference characters indicate corresponding parts throughout the several views. Although the drawings represent embodiments of various features and components according to the present invention, the drawings are not necessarily to scale and certain features may be exaggerated in order to better illustrate and explain the present invention. The exemplification set out herein illustrates embodiments of the invention, and such exemplifications are not to be construed as limiting the scope of the invention in any manner.

DETAILED DESCRIPTION OF EMBODIMENTS OF THE INVENTION

Concepts described below may be further explained in one of more of the co-filed patent applications entitled HELP UTILITY FUNCTIONALITY AND ARCHITECTURE, application Ser. No. 11/999,906, METHOD AND SYSTEM FOR GRAPHICALLY INDICATING MULTIPLE DATA VALUES, application Ser. No. 11/999,853, SYSTEM AND METHOD FOR DATABASE INTEGRITY CHECKING, application Ser. Nos. 11/999,856 and 13/293,063, METHOD AND SYSTEM FOR DATA SOURCE AND MODIFICATION TRACKING, application Ser. No. 11/999,888, PATIENT-CENTRIC HEALTHCARE INFORMATION MAINTENANCE, application Ser. Nos. 11/999,874 and 13/162,168, EXPORT FILE FORMAT WITH MANIFEST FOR ENHANCED DATA TRANSFER, application Ser. No. 11/999,867, GRAPHIC ZOOM FUNCTIONALITY FOR A CUSTOM REPORT, application Ser. No. 11/999,932, METHOD AND SYSTEM FOR SELECTIVE MERGING OF PATIENT DATA, application Ser. No. 11/999,859, METHOD AND SYSTEM FOR PERSONAL MEDICAL DATA DATABASE MERGING, application Ser. No. 11/999,772, METHOD AND SYSTEM FOR WIRELESS DEVICE COMMUNICATION, application Ser. No. 11/999,879, METHOD AND SYSTEM FOR SETTING TIME BLOCKS, application Ser. No. 11/999,968, METHOD AND SYSTEM FOR ENHANCED DATA TRANSFER, application Ser. Nos. 11/999,911 and 13/195,534, COMMON EXTENSIBLE DATA EXCHANGE FORMAT, application Ser. No. 11/999,871, METHOD OF CLONING SERVER INSTALLATION TO A NETWORK CLIENT, application Ser. No. 11/999,876, METHOD AND SYSTEM FOR QUERYING A DATABASE, application Ser. No. 11/999,912, METHOD AND SYSTEM FOR EVENT BASED DATA COMPARISON, application Ser. No. 11/999,921, DYNAMIC COMMUNICATION STACK, application Ser. Nos. 11/999,934 and 13/782,501, SYSTEM AND METHOD FOR REPORTING MEDICAL INFORMATION, application Ser. No. 11/999,878, METHOD AND SYSTEM FOR MERGING EXTENSIBLE DATA INTO A DATABASE USING GLOBALLY UNIQUE IDENTIFIERS, application Ser. No. 11/999,947, METHOD AND SYSTEM FOR ACTIVATING FEATURES AND FUNCTIONS OF A CONSOLIDATED SOFTWARE APPLICATION, application Ser. No. 11/999,880, METHOD AND SYSTEM FOR CONFIGURING A CONSOLIDATED SOFTWARE APPLICATION, application Ser. No. 11/999,894, METHOD AND SYSTEM FOR DATA SELECTION AND DISPLAY, application Ser. No. 11/999,896, METHOD AND SYSTEM FOR CREATING REPORTS, application Ser. No. 11/999,851, METHOD AND SYSTEM FOR CREATING USER-DEFINED OUTPUTS, application Ser. No. 11/999,905, DATA DRIVEN COMMUNICATION PROTOCOL GRAMMAR, application Ser. No. 11/999,770, HEALTHCARE MANAGEMENT SYSTEM HAVING IMPROVED PRINTING OF DISPLAY SCREEN INFORMATION, application Ser. No. 11/999,855, and METHOD AND SYSTEM FOR MULTI-DEVICE COMMUNICATION, application Ser. Nos. 11/999,866 and 13/150,398, the entire disclosures of which are hereby expressly incorporated herein by reference. It should be understood that the concepts described below may relate to diabetes management software systems for tracking and analyzing health data, such as, for example, the ACCU-CHEK® 360° product provided by Roche Diagnostics. However, the concepts described herein may also have applicability to apparatuses, methods, systems, and software in fields that are unrelated to healthcare. Furthermore, it should be understood that references in this patent application to devices, meters, monitors, pumps, or related terms are intended to encompass any currently existing or later developed apparatus that includes some or all of the features attributed to the referred to apparatus, including but not limited to the ACCU-CHEK® Active, ACCU-CHEK® Aviva, ACCU-CHEK® Compact, ACCU-CHEK® Compact Plus, ACCU-CHEK® Integra, ACCU-CHEK® Go, ACCU-CHEK® Performa, ACCU-CHEK® Spirit, ACCU-CHEK® D-Tron Plus, and ACCU-CHEK® Voicemate Plus, all provided by Roche Diagnostics or divisions thereof.

For the purposes of promoting an understanding of the principles of the invention, reference will now be made to the embodiments illustrated in the drawings, which are described below. The embodiments disclosed below are not intended to be exhaustive or limit the invention to the precise form disclosed in the following detailed description. Rather, the embodiments are chosen and described so that others skilled in the art may utilize their teachings. It will be understood that no limitation of the scope of the invention is thereby intended. The invention includes any alterations and further modifications in the illustrated devices and described methods and further applications of the principles of the invention which would normally occur to one skilled in the art to which the invention relates.

The present invention relates to a method and system for associating database content. The system comprises a computer, applications, and databases. An application, computer program, or program, is here, and generally, conceived to be a sequence of computer instructions representing steps of methods for achieving desired results. The instructions are processed by a computer and require physical manipulations of physical quantities. Usually, though not necessarily, these quantities take the form of electrical or magnetic signals capable of being stored, transferred, combined, compared, and otherwise manipulated. Programs may use data structures for both inputting information and producing the desired result. Data structures impart a physical organization on the data stored in computer memory and greatly facilitate data management. Databases include data structures and data.

The actual physical implementation of a database on a general purpose computer may take several forms, from complete individual records storing the substantive information with several key indexes for locating a particular record, to a plurality of tables interrelated by relational operations, to a matrix of cross-linked data records, to various combinations and hybrids of these general types. In particular physical devices, a database may be structured and arranged to accommodate the restrictions of the physical device but, when transferred to a general purpose computer, be able to be stored in a variety of formats. Thus, while certain types of information may be described as being stored in a "database" from a conceptual standpoint, generally such information may be electronically stored in a variety of structures with a variety of encoding techniques.

Figure 1:
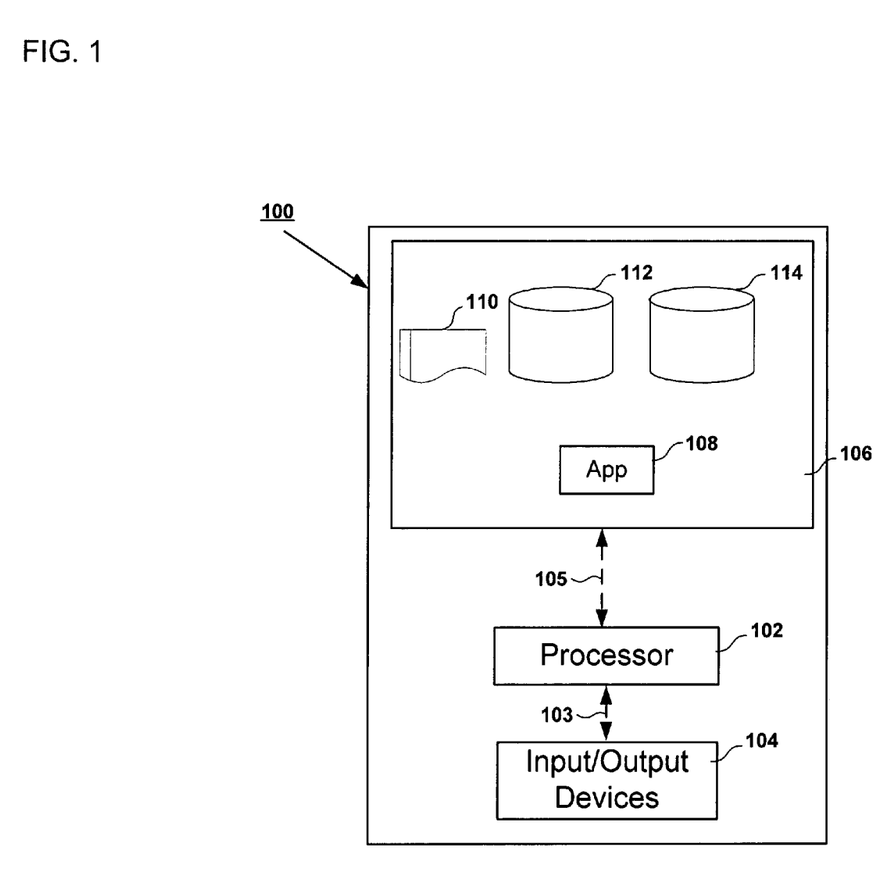
FIG. 1 is a conceptual diagram of a system according to the invention depicting a computer, a data management application, a key store, and databases.

Turning now to the figures, FIG. 1 depicts an exemplary embodiment of a system according to the invention. The system comprises computer 100 having processor 102 in logical communication with input/output devices 104 by means of communication lines 103, and with storage media 106 by means of communication lines 105. A processing unit, or processor, may be any circuit or its equivalent capable of interpreting instructions or performing logical actions on information. Input devices include a mouse and a keyboard although computer 100 may comprise any input device. An output device includes a video screen although computer 100 may comprise any output device. While described and depicted herein with specific reference to a computer, the present invention may be utilized in conjunction with any device capable of processing programs that access databases including without limitation a blood glucose meter, an infusion pump, or an integrated device including a glucose measurement engine or an infusion pump.

Computer 100 may include communications media for receiving patient data from medical devices. Medical devices are devices capable of recording patient data and transferring data to software. While the invention is described herein with reference to medical devices, and more particularly, with reference to diabetes management devices, the invention is applicable to any data obtained from any device. Medical devices may include monitors which record values of measurements relating to a patient's physiological condition and information such as the time and date when the measurement was recorded. Medical devices may also be devices configured to provide medications to patients such as, for example, insulin pumps. These devices, generally, record dosage amounts as well as the time and date when the medication was provided. Optionally, medical devices may have their own input devices and display devices. Medical devices may transfer data to computer 100 through ports configured to establish a physical connection or through communication media such as a modulated signal transceiver configured to transmit and receive a modulated signal. A medical device may also comprise computer 100 integrated or coupled with a device for recording medical data including without limitation a computer, personal digital assistants (PDAs), phones, and BLACKBERRYs. Methods for downloading data from medical devices are disclosed in the above-identified co-filed patent applications.

Computer 100 may include a variety of computer-readable media. Computer-readable media can be any available media that can be accessed by computer 100 and includes storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store the desired information and which can be accessed by computer 100. Computer-readable media may be accessed directly or through a network or the Internet.

The communication media is typically embodied by hardware for conveying data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct wired connection, and wireless media such as acoustic, RF, infrared and other wireless media. Combinations of any of the above are included within the scope of communication media.

Computer 100 may operate in a network environment using logical connections to one or more remote computers. The remote computer may be a personal computer, a server, a network PC, and typically includes many or all of the elements described above relative to computer 100. The logical connections include a local area network (LAN) and a wide area network (WAN), but also include other networks. The terms "network," "local area network," "LAN," "wide area network," or "WAN" mean two or more computers which are connected in such a manner that messages may be transmitted between them. Such network environments are commonplace in office, enterprise-wide computer networks, Intranets, and the Internet. In such computer networks, typically one or more computers operate as a "server," a computer with large storage media such as hard disk drives and communication hardware to operate peripheral devices such as printers or modems. Other computers, termed "clients" or "workstations," provide a user interface so that users of computer networks can access the network resources, such as shared data files, common peripheral devices, and inter-workstation communication. The computers have at least one processor for executing machine instructions, and memory for storing instructions and other information. Many combinations of processing circuitry and information storing equipment are possible.

A particular embodiment of a system according to the invention is the ACCU-CHEK® 360° diabetes management system distributed by Roche Diagnostics Corporation. The ACCU-CHEK® 360° databases and programs may be installed in a computer comprising a stand-alone computer or may be installed on a server. The system may download data from medical devices and may merge data from other databases. For example, a user who had been using another system may choose to upgrade to an ACCU-CHEK® 360° system. The ability to merge data allows the user to use the old data. Methods for merging data are disclosed in the above-identified co-filed patent applications. The ACCU-CHEK® 360° system may also receive medical data from multiple patients. The ACCU-CHEK® 360° software may be installed to operate in one of many languages.

Privacy concerns require that certain information relating to individuals, and in the case of healthcare management, patients, be protected. Because security may differ according to the database content, it may be desirable to segregate data into a plurality of databases. In healthcare data management, the term "patient" refers to a person whose medical information is stored in the system. As used herein, patient data refers to data that can identify a patient including administrative data such as name, address, phone number, and medical data such as physiological parameter values including without limitation blood glucose values, A1c values, Albumin values, Albumin excretion values, body mass index values, blood pressure values, carbohydrate values, cholesterol values (total, HDL, LDL, ratio) creatinine values, fructosamine values, HbA1 values, height values, insulin dose values, insulin rate values, total daily insulin values, ketone values, microalbumin values, proteinuria values, heart rate values, temperature values, triglyceride values, and weight values. Patient data may be provided by the patient, a healthcare professional, a medical device, a caregiver, or anyone having relevant data pertaining to a patient.

The system includes application 108 for managing data, an encryption key for encrypting data, and two or more databases 112, 114 for storing encrypted data. Databases may be stored locally in storage devices including a stand-alone computer storage device and a client storage device, or remotely in remote storage devices including a remote computer and a server, or both locally and remotely. Encrypted data may include application user access data, patient data, and other data including application settings, application configuration, administrative, and other data. As used herein, application user access data means user access data required to use application 108 which should be distinguished from computer user access data which may required to gain access to computer 100 or client 100'. In one embodiment, the databases are relational databases and the database server is the MICROSOFT SQL Server Express 2005. Computer 100 may include other applications required for operation of the SQL Server.

The encryption key may stored in key store 110 which may reside in local or remote storage. As used herein, a key store is a storage location for the encryption key. Key store 100 may be, without limitation, an operating system key store, a key server appliance or vault, removable media, e.g., a dongle, and a file. If key store 100 is a file, the file may be encrypted to protect the application 108 encryption key. Furthermore, the encryption key may be obtained by a user and stored externally of the system, e.g., written down or in a user's memory. In the latter cases, the data management application 108 prompts the user to provide the encryption key to access the encrypted data.

In one embodiment of the system according to the invention, storage media 106 stores data management application 108, system database 112, one or more results database 114, and key store 110. Storage media 106 is in logical communication with processor 102 by means of communication lines 105. Application 108 is provided to manage data stored in databases 112, 114 residing locally in computer 100. System database 112 is associated with results database 114 by an encryption key stored in key store 110. Application 108 may permit multiple users. Each user has application user access data, e.g., i.d. and password, necessary to use application 108. Application user access data is encrypted with the encryption key to limit use of application 108 to authorized users. Encrypted application user access data may be stored in system database 112 or results database 114.

The encryption key enables encryption/decryption of data stored in the databases, e.g., system database 112 and results database 114. In one embodiment, system database 112 contains data including encrypted user access data. System database 112 can have any structure sufficient to store and retrieve application encrypted user access data including without limitation a relational database, a flat file, and a binary data file. System database 112 may also store user preferences pertaining to application 108 settings. Application 108 has default settings for selecting menu screens, graphs, reports and so on. Users may change default settings, and the changed settings may be stored in system database 112. In another embodiment, results database 114 contains data including encrypted user access data and patient data.

In another embodiment of a system according to the invention, computer 100 comprises a Windows operating system and uses Windows security features to enable a user to access application 108. The user i.d. and password required by Windows may pass-through to application 108 to enable access to key store 110 and, consequently, to databases 112, 114.

Installation of application 108 on computer 100 may involve selection of choices that impact settings, features, associations, and other variables that impact operation of application 108. An installer application, not shown, installs application 108, databases 112, 114, and key store 110 in computer 100. The installer may be provided in removable storage media including a CD, DVD, or USB thumbdrive or key. The encryption key may be created by the installer application or by application 108 after the installation is complete.

The encryption key may also be created before or during installation of programs, files, and databases.

In another embodiment of the method according to the invention, application 108 may access multiple results databases. In an exemplary embodiment, the results databases were described as a single database 114. However, the invention is not so limited, and the system may comprise more than one results database. Additional databases may be created to distribute storage of patient data. Application 108 may create additional results databases configured to store encrypted data. Alternatively, the installer may be used to create additional results databases. In both cases, the same encryption key secures all databases accessed by application 108.

The encryption key for each installation of application 108 is unique. Preferably, the encryption key is generated by a random cryptographic function. Because the encryption key is unique, a first and second system according to the invention, equally configured, cannot access the other system's data. The first system's encryption key enables access to only the first system's databases. The second system's encryption key enables access only to the second system's databases. While the first and second systems have thus far been described in the context of a stand-alone computer 100, the same enhanced security results when application 108 is installed in a client/server network environment.

Figure 2:
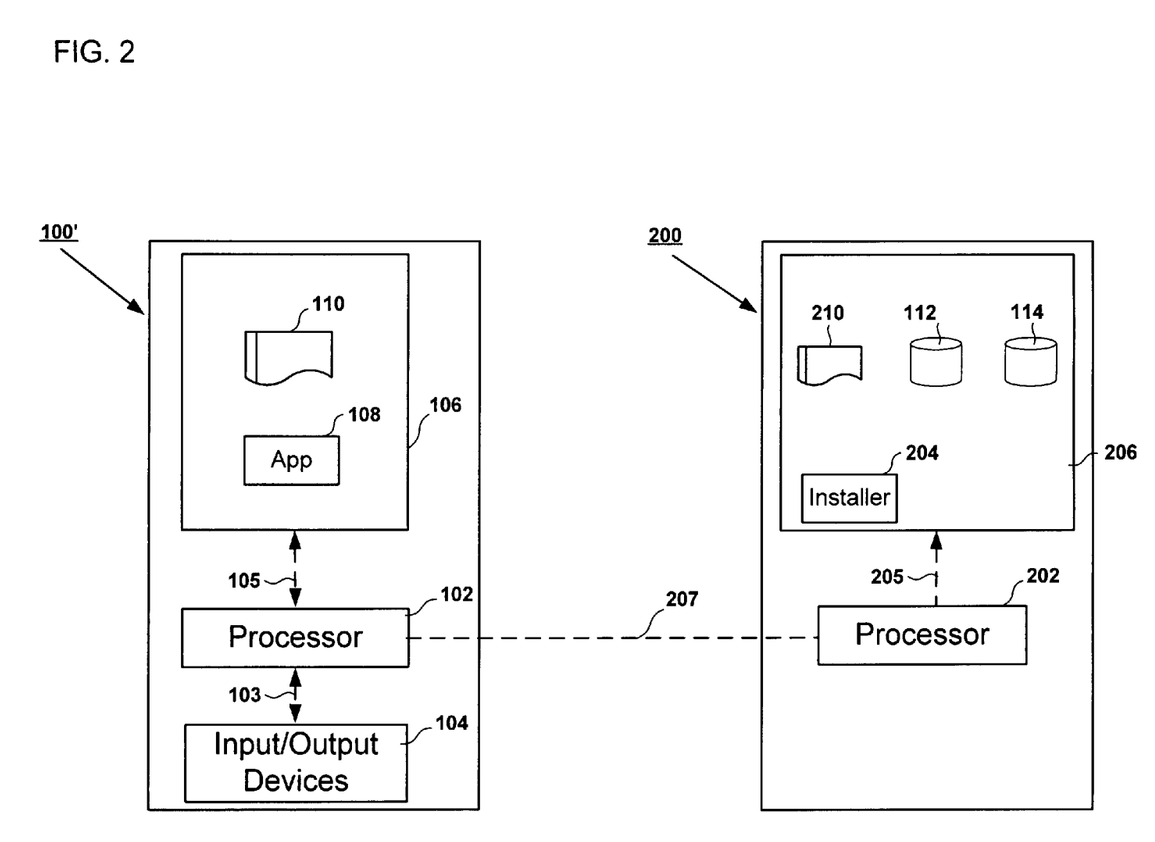
FIG. 2 is a conceptual diagram of a system according to the invention depicting a client computer, a server computer, a data management application, key stores, a replicated installer application, and databases.

Referring now to FIG. 2, another exemplary embodiment of a system according to the invention is provided. The system operates in a client/server environment over a network. Client 100' has processor 102 in logical communication with input/output devices 104 by means of communication lines 103, and with storage media 106 by means of communication lines 105. Application 108 resides in storage media 106. Generally, client 100' is similar to computer 100. Server 200 has processor 202 in logical communication with server storage media 206 by means of communication lines 205. Optional key store 210 and databases 112, 114 reside remotely in server storage media 206. Network communications, represented by communication lines 207, enable communication between server processor 202 and client processor 102 thereby enabling data access by application 108 to databases 112, 114 in server storage media 206. Databases 112, 114 are associated by a common encryption key stored in key store 110 in storage media 106. Alternatively, the common encryption key is stored in key store 210 in storage media 206.

Figure 3:
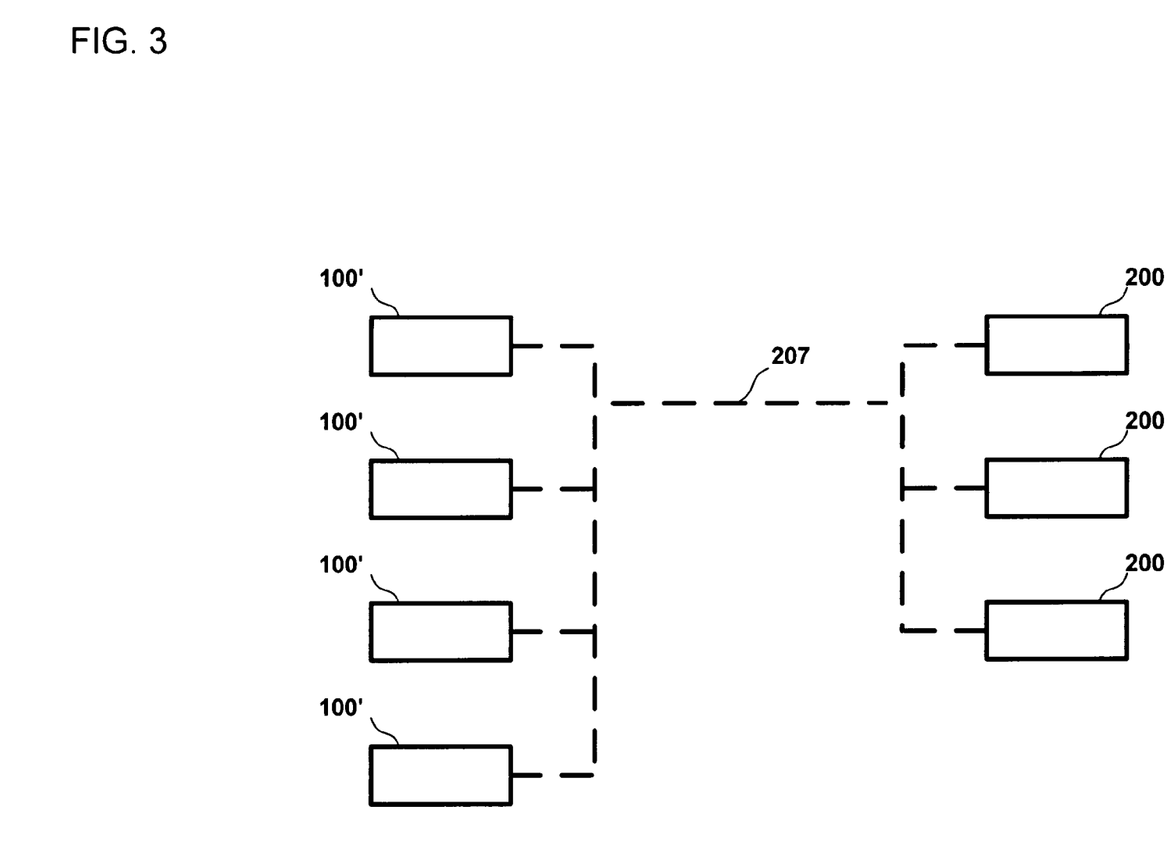
FIG. 3 is a conceptual diagram of a system according to the invention depicting a plurality of client computers and server computers.

Referring now to FIG. 3, another exemplary embodiment of a system according to the invention is provided. A plurality of clients 100' are installed on a network. One or more servers 200 are provided. An extensive client/server installation with multiple applications 108 might be desirable in a healthcare facility such as a hospital where physicians may desire control of the data and the benefits of remote storage on a facility's network. Physicians might also desire to access some data on the local computer for various reasons including perhaps faster access or better reliability. Patient data used to treat patients may require different care than patient data used to perform group or population studies and, therefore, might be subject to different storage requirements. Databases may be installed locally or remotely in any of clients 100' and servers 200. As disclosed herein, enhanced security limits access of a client 100' application 108 to databases installed with the associated encryption key. Only an user with access to a specific client 100' can access results database 114 or create more results databases with the key corresponding to the specific client 100'.

Installation of application 108 and databases 112, 114 on clients 100' and servers 200 may involve selection of choices that impact settings, features, associations, and other variables that impact operation of application 108. In some network/client installations of application 108, consistent and uniform operation on one or more of the installations is desired. Such consistent and uniform operation may be achieved by making identical selections during installation of each application 108. Custom designation of associations, such as selection of a database on a connected server, may be accomplished by providing input or making a selection of a provided option.

The installer program previously discussed may install the programs, files and databases directly in client 100'. Alternatively, the installer may replicate itself in server 200 as installer 204. Subsequent client 100' installations of applications 108, key stores 110, and databases 112, 114 are achieved by selecting replicated installer 204 on server system 200. This selection may be made via a shortcut pushed or pulled down to client 100', by navigating to client system 100' over the network, or otherwise. A method for installing applications over a network is disclosed in the above-identified co-filed patent applications. As previously discussed, the installer creates an encryption key and stores it in key store 110.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

The invention claimed is:

1. A method for associating database content comprising the steps of:

providing a computing system including a storage media;

installing an application in the storage media adapted to access and manipulate medical records of a patient;

providing a first encryption key stored in a computer readable media, the first encryption key accessible by the application;

encrypting user access data including a user identification and password with the first encryption key and storing the encrypted user access data in a system database that comprises, encrypting a plurality of user data, each of the plurality of user data associated with a unique command, providing a second encryption key stored in a computer readable media, the second encryption key also accessible by the application, encrypting a second plurality of medical records with the second encryption key and storing the encrypted second plurality of medical records in a results database, and encrypting a second user access data, the second user access data associated with a second command, wherein the application responds to input of the second command associated with the second user access data by accessing the second encryption key and the second encryption key decrypting the second user access data, wherein the application identifies the second command as being associated with an authorized user based on the decrypted second user access data and provides the authorized user access to utilize the application for accessing the second plurality of medical records;

encrypting a plurality of medical records with the first encryption key and storing the encrypted medical records in a results database embedded in the storage media of the computing device and the second plurality of medical records encrypted with the second encryption key is stored in a results database embedded in a remote storage media; and inputting a command requesting rights to utilize the application for accessing the medical records, wherein the application responds to the step of inputting by accessing the first encryption key and decrypting the user access data, wherein the application identifies the command as being associated with an authorized user based on the decrypted user access data and provides the authorized user access to utilize the application for accessing the plurality of medical records encrypted with the first encryption key.

2. The method of claim 1 wherein the first encryption key is stored in a key store.

3. The method of claim 2 wherein the key store is selected from a group consisting of an operating system key store and a key server appliance, removable media, and a file.

4. The method of claim 1 wherein the system database is embedded in the storage media and the results database is embedded in a remote storage media.

5. The method of claim 1 wherein a plurality of results databases are embedded in a remote storage media and are accessible by the application.

6. The method of claim 1 wherein the command, input in the step of inputting, comprises a log-in ID.

7. The method of claim 1 further including the steps of:
providing a second encryption key stored in a computer readable media, the second encryption key also accessible by the application;
encrypting a second plurality of medical records with the second encryption key and storing the encrypted second plurality of medical records in a results database; and
encrypting a second user access data, the second user access data associated with a second command, wherein the application responds to input of the second command associated with the second user access data by accessing the second encryption key and the second encryption key decrypting the second user access data, wherein the application identifies the second command as being associated with an authorized user based on the decrypted second user access data and provides the authorized user access to utilize the application for accessing the second plurality of medical records.

8. The method of claim 7 wherein the encrypted second plurality of medical records and the plurality of medical records encrypted by the first encryption key are stored in the same results database.

9. The method of claim 1 wherein the application, upon identifying the command as associated with an authorized user, further provides the authorized user access to the application for manipulating the medical records encrypted with the first encryption key.

10. The method of claim 1, wherein the step of encrypting the plurality of medical records comprises encrypting a first medical record prior to encrypting a second medical record.

* * * * *